(12) United States Patent
Holla

(10) Patent No.: US 6,406,912 B1
(45) Date of Patent: Jun. 18, 2002

(54) METHOD FOR ENZYMATIC ENANTIOMER-SEPARATION OF 3(R)- AND 3(S)-HYDROXY-1-METHYL-4-(2,4,6-TRIMETHOXYPHENYL)-1,2,3,6-TETRAHYDRO-PYRIDINE OR ITS CARBOXYLIC ACID ESTERS

(75) Inventor: Wolfgang Holla, Kelkheim (DE)

(73) Assignee: Aventis Pharma Deutshland GmbH, Frankfurt am Main (DE)

( * ) Notice: Subject to any disclaimer, the term of this patent is extended or adjusted under 35 U.S.C. 154(b) by 0 days.

(21) Appl. No.: 09/623,563

(22) PCT Filed: Feb. 20, 1999

(86) PCT No.: PCT/EP99/01113

§ 371 (c)(1),
(2), (4) Date: Sep. 6, 2000

(87) PCT Pub. No.: WO99/45133

PCT Pub. Date: Sep. 10, 1999

(30) Foreign Application Priority Data

Mar. 6, 1998 (DE) .......................................... 198 09 649

(51) Int. Cl.[7] .................... C07D 213/80; C07D 213/78; C12N 5/00
(52) U.S. Cl. ....................... 435/814; 435/816; 546/300; 546/301; 546/302
(58) Field of Search ................................. 435/814, 816; 546/300, 301, 302

(56) References Cited

U.S. PATENT DOCUMENTS 4,971,909 A  11/1990  Kaneoya et al.
6,225,473 B1 *  5/2001  Breipohl et al. ............ 546/185

FOREIGN PATENT DOCUMENTS

EP  0 321 918  6/1989
EP  0 474 129  3/1992
EP  0 507 278  10/1992

OTHER PUBLICATIONS

Database WPI, Section Ch. Week 9418, Class 803, AN 94–147005, XP002105673 & JP 06 090790 A (5APR94), Czech et al., "Antitumoral Activity of Flavone L 86–8275," International Journal of Oncology, vol. 6, pp. 31–36 (1995).
Sedlacek et al., "Flavopiridol (L86 8275; NSC 649890), a New Kinase Inhibitor for Tumor Therapy," International Journal of Oncology, vol. 9 pp. 1143–1168 (1996).

* cited by examiner

Primary Examiner—Alan L. Rotman
(74) Attorney, Agent, or Firm—Finnegan, Henderson Farabow, Garrett & Dunner, LLP

(57) ABSTRACT

The invention relates to a method for producing optically pure compounds of 3(R)- and 3(S)-hydroxy-1-methyl-4-(2,4,6-trimethoxyphenyl)-1,2,3,6-tetrahydro-pyridine or its carboxylic acid esters by reacting the enantiomer mixtures stereoselectively, using an enzyme.

6 Claims, No Drawings

METHOD FOR ENZYMATIC ENANTIOMER-SEPARATION OF 3(R)- AND 3(S)-HYDROXY-1-METHYL-4-(2,4,6-TRIMETHOXYPHENYL)-1,2,3,6-TETRAHYDRO-PYRIDINE OR ITS CARBOXYLIC ACID ESTERS

This application is a national stage filing under 35 U.S.C. §371 of international application No. PCT/EP99/01113, filed on Feb. 20, 1999.

Process for the enzymatic separation of enantiomers of 3(R)- and 3(S)-hydroxy-1-methyl-4-(2,4,6-trimethoxyphenyl)-1,2,3,6-tetrahydropyridine or of the carboxylic acid esters.

The invention relates to a process for the preparation of optically pure compounds of the formula (I) by stereodifferentiating reaction of the mixtures of enantiomers with the aid of an enzyme.

3(S)- and 3(R)-hydroxy-1-methyl4-(2,4,6-trimethoxyphenyl)-1,2,3,6-tetrahydropyridine (compounds of the formula (I) where R=H) or their ester derivatives (compounds of the formula (I) where $R=COR^1$) are central units or precursors of the synthesis of flavopiridol (HMR 1275 or L 86 8275) described in the patent application No. HMR 98/L 001 ("Process for the preparation of (−)cis-3-hydroxy-1-methyl-4(R)-(2,4,6-trimethoxy-phenyl) piperidine)"), of the first potent inhibitor of cyclin-dependent protein kinase (see, for example, Sedlacek, Hans Harald; Czech, Joerg; Naik, Ramachandra; Kaur, Gurmeet; Worland, Peter; Losiewicz, Michael; Parker, Bernard; Carlson, Bradley; Smith, Adaline; et al. Flavopiridol (L 86 8275; NSC 649890), a new kinase inhibitor for tumor therapy, Int. J. Oncol. (1996), 9(6), 1143–1168 or Czech, Joerg; Hoffmann, Dieter; Naik, Ramachandra; Sedlacek, Hans-Harald; Antitumoral activity of flavone L 86 8275. Int. J. Oncol. (1995), 6(1), 31–36).

A resolution of racemates or separation of enantiomers of the compounds of the formula (I) is not known.

It has now been found that compounds of the formula (I) can be obtained in optically pure form from the mixtures of enantiomers by enzymatic ester cleavage (hydrolysis or alcoholysis).

The present invention thus relates to a process for the kinetic resolution of racemates of compounds of the formula (I),

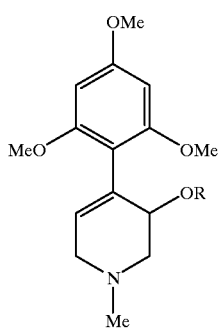

(I)

which comprises subjecting enantiomer mixtures or racemic mixtures of compound s of the formula (I), in which R is $COR^1$ where $R^1=(C_1–C_{16})$-alkyl, $(C_2–C_{16})$-alkenyl or $(C_3–C_{16})$-alkynyl, $C_nH_{2n}$-cycloalkyl where n=1–16, which can be branched or unbranched and which can be substituted by 1–3 substituents from the group F, Cl, Br, I, $CF_3$, CN, $NO_2$, hydroxyl, methoxy, ethoxy and $COOR^2$, where $R^2=(C_1–C_4)$-alkyl and $(C_2–C_4)$-alkenyl, which can be branched or unbranched and which can be substituted by 1–3 substituents from the group consisting of F, Cl, Br, $CF_3$, in homogeneous or heterogeneous, aqueous, aqueous/organic or organic media in the presence of an enzyme, e.g. of a lipase or esterase, e.g. from mammalian livers or pancreases or microbial origin, such as, for example, from Candida, Pseudomonas and Aspergillus, or of a protease, e.g. from Bacillus, to a stereoselective hydrolysis or alcoholysis at a temperature of 10–80° C., if appropriate in the presence of cosolvents and of a buffer, the reaction mixture preferably containing 2–50% by weight of ester and, after the reaction has taken place, separating the unreacted ester (compound of the formula (I) where $R=COR^1$) and the alcohol formed (compound of the formula (I) where R=H)—and thus the two enantiomers.

The process according to the invention is economical, simple and rapid. The reaction does not require any equimolar amounts of optically pure auxiliaries, any expensive reagents, any disproportionately large amounts of solvent and any cost-intensive working steps. After the completion of the reaction, the separation of the products or of the enantiomers can be carried out by simple measures, e.g. by extraction.

Preferably, in the compounds of the formula (I)
R is $COR^1$ where $R^1=(C_1–C_{12})$-alkyl, $(C_2–C_{12})$-alkenyl or $(C_3–C_{12})$-alkynyl, $C_nH_{2n}$-cycloalkyl where n=1–12, which can be branched or unbranched and which can be substituted by 1–3 substituents from the group consisting of F, Cl, Br, $CF_3$, CN, $NO_2$, hydroxyl, methoxy, ethoxy and $COOR^2$, where $R^2$=methyl, ethyl and vinyl, which can be substituted by 1–3 substituents from the group consisting of F, Cl, $CF_3$.

Particularly preferably, in the compounds of the formula (I)
R is $COR^1$ where $R^1=(C_1–C_{10})$-alkyl, $(C_2–C_{10})$-alkenyl or $(C_3–C_{10})$-alkynyl, $C_nH_{2n}$-cycloalkyl where n=1–10, which can be branched or unbranched and which can be substituted by 1–3 substituents from the group consisting of F, Cl, Br, $CF_3$, CN, $NO_2$, methoxy, and $COOR^2$, where $R^2$=methyl, ethyl and vinyl, which can be substituted by 1–3 substituents from the group consisting of F, Cl, $CF_3$.

Very particularly preferably, in the compounds of the formula (I)
R is $COR^1$ where $R^1=(C_1–C_{10})$-alkyl, $(C_2–C_{10})$-alkenyl or $(C_3–C_{10})$-alkynyl,
which can be branched or unbranched and which can be substituted by 1–3 substituents from the group consisting of F, Cl, Br, $CF_3$, and methoxy.

A procedure is preferably used in the process in which an ester of the formula (I), for example $R=COR^1$ where $R^1=C_3H_7$ or $C_8H_{17}$, is treated with a lipase, esterase or protease in a water- or alcohol-containing solution and stirred. It may be advantageous to buffer the solution mentioned, e.g. with phosphate or TRIS [=tris (hydroxymethyl)-methylamine] buffer. The addition can be, for example, 0.01–1.0 molar. A suitable buffer range is pH 5–9.

It may furthermore be advantageous to add cosolvents. Suitable cosolvents are, for example, dimethoxyethane, acetone, THF, dioxane, hexane, tert-butyl methyl ether and tert-butanol. The proportion of cosolvents in the solution is preferably 10–80%.

The enzymes employed are preferably lipases and esterases, such as, for example, cholesterol esterase (EC 3.1.1.13) from bovine pancreas (Sigma Chemical Co.), porcine liver esterase (PLE, Sigma Chemical Co.), pancreatin (Fluka and Sigma Chemical Co.), pancreas acetone powder from cattle (Sigma Chemical Co.), liver acetone powder from horses (Sigma Chemical Co.) and lipase from porcine pancreas (PPL, Sigma Chemical Co.), lipase OF from Candida rugosa (Meito Sangyo) and lipase AP-6 from Aspergillus niger (Amano Pharmaceuticals).

Each of the enzymes mentioned can be employed in free or in immobilized form (Immobilized Biocatalysts, W. Hartmeier, Springer Verlag Berlin, 1988). The amount of enzyme is freely selected depending on the reaction rate or on the reaction time desired and on the nature of the enzyme (e.g. free or immobilized) and is easy to determine by simple preliminary experiments.

The reaction mixture preferably contains 2–50% by weight of ester, particularly preferably 5–20%. The reaction temperature is 10–80° C., preferably 20–60° C., particularly preferably 20–40 ° C.

The preparation of the esters (compounds of the formula (I) where $R=COR^1$) is expediently carried out from the alcohol (compound of the formula I where R=H) according to known methods of esterification (Haslam, Tetrahedron 1980, 36, 2409; Höfle, Steglich, Vorbrüggen, Angew. Chem. 1978, 90, 602) or as described in the patent application HMR 98/L 001 ("Process for the preparation of (–)cis-3-hydroxy-1-methyl-4(R)-(2,4,6-trimethoxyphenyl)piperidine").

The products resulting from or remaining in the process can be separated in a simple manner, e.g. by extraction or chromatographic methods. The remaining ester is obtained, for example, by partitioning the reaction solution between water and n-heptane and concentrating the organic phase. The resulting alcohol can then be extracted from the aqueous phase with ethyl acetate. The enzyme can be recovered by freeze-drying. The separation (and, if appropriate, later reuse) of the enzyme can be facilitated by immobilization.

By means of suitable conduct of the reaction, it is always possible to obtain at least one enantiomer optically pure. If optically pure ester is desired, the conversion should be over (or equal to) 50%, if optically pure alcohol is desired, the conversion should be smaller (or equal to) 50%. The conversion of the enzymatic hydrolysis or alcoholysis was determined using HPLC (RP 18 LiChrosorb®) and the determination of the optical purity was carried out by HPLC (Chiralpak AD). The esters resulting from or remaining in the racemate resolution process can be converted into the corresponding alcohol without inversion or racemization by known methods of ester cleavage (S. J. Salomon, E. G. Mata, O. A. Mascaretti, Tetrahedron 1993, 49, 3691–3748). Conversely, the resulting alcohol can be converted into the corresponding ester without inversion or racemization by known methods of esterification (Haslam, Tetrahedron 1980, 36, 2409).

The products resulting from or remaining in the process can be racemized and employed again in the racemate resolution according to known methods, e.g. by metal-catalyzed rearrangements (L. E. Overman, Angew. Chem. 1984, 96, 565–573 and literature already cited). This increases the yield to over 50%. For example, the compounds of the formula (I) where $R=COR^1$ can be racemized directly and those of the formula (I) where R=H can be racemized, for example, after conversion into suitable derivatives, such as described in L. E. Overman, Angew. Chem. 1994, 96, 565–573. Metal catalysts which can be used are, for example, Hg(II), Pd(O) or Pd(II) compounds or salts.

The present invention is intended to be illustrated in greater detail by means of the following examples.

EXAMPLES

All isolated products or crude product mixtures were identified by $^1$H-NMR and mass spectra or by HPLC.

The optical purity of the products was determined by HPLC, e.g. on Chiralpak AD 250×4.6 (Daicel).

Example 1

10 mg of the acetic acid ester [compound of the formula I where $R^1=COR^2$ and $R^2=COCH_3$] were introduced into 1 ml of potassium phosphate buffer (0.1 M, pH=7.0)/dimethoxyethane (5:1). 5 mg of pancreatin were added. The mixture was stirred at 20–25° C. until the conversion had reached about 40% (HPLC). It was then filtered, concentrated to dryness and the resulting mixture was investigated by HPLC (Chiralpak AD 250×4.6, n-hexane+EtOH 5+1, flow 1 ml/min, 25° C., 220/240 nm): ee of the remaining (R)-acetic acid ester: 63%; ee of the (S)-alcohol: 85%.

Example 2

10 mg of the butyric acid ester [compound of the formula I where $R^1=COR^2$ and $R^2=CO(CH_2)_2CH_3$] were introduced into 1 ml of potassium phosphate buffer (0.1 M, pH=7.0)/dimethoxyethane (5:1). 5 mg of PPL (lipase from porcine pancreas, Sigma Chemical Co.) were added. The mixture was stirred at 30° C. until the conversion had reached about 48% (HPLC). It was then filtered, concentrated to dryness and the resulting mixture was investigated by HPLC (Chiralpak AD 250×4.6, n-hexane+EtOH 6+1, flow 1 ml/min, 25° C., 220/240 nm): ee of the (R)-butyric acid ester: 90%; ee of the (S)-alcohol: 97%.

Example 3

1.0 g (2.86 mmol of the butyric acid ester [compound of the formula I where $R^1=COR^2$ and $R^2=CO(CH_2)_2CH_3$] were introduced into 8 ml of dimethoxyethane and 40 ml of potassium phosphate buffer (0.1 M, pH=7.0). 90 mg of pancreatin were added. The mixture was stirred at 22–25° C. until the conversion had exceeded 50%. It was then concentrated in vacuo, mixed with water and extracted six times with about 50 ml of n-heptane. After drying ($Na_2SO_4$), it was concentrated in vacuo. 450 mg (45%) of the (R)-butyric acid ester were obtained; ee (HPLC):>99%. After extraction of the remaining aqueous phase with ethyl acetate, drying ($Na_2SO_4$) and concentrating in vacuo, 190 mg (23.8%) of the (S)-alcohol were obtained; ee (HPLC): 97%.

Example 4

10 mg of the butyric acid ester [compound of the formula I where $R^1=COR^2$ and $R^2=CO(CH_2)_2CH_3$] were introduced into 1 ml of potassium phosphate buffer (0.1 M, pH=7.0)/dimethoxyethane (5:1). 5 mg of PPL were added. The mixture was stirred at 30° C. until a conversion of about 48% (HPLC) was reached. It was then filtered, concentrated to dryness and the resulting mixture was investigated by HPLC (Chiralpak AD 250×4.6, n-hexane+EtOH 6+1, flow 1 ml/min, 25° C., 220/240 nm): ee of the (R)-butyric acid ester: 90%; ee of the (S)-alcohol: 97%. Example 5

10 mg of the butyric acid ester [compound of the formula I where $R^1=COR^2$ and $R^2=CO(CH_2)_2CH_3$] were introduced into 1 ml of potassium phosphate buffer (0.1 M, pH=7.0)/dimethoxyethane (5:1). 5 mg of PLE (porcine liver esterase, Sigma Chemical Co.) were added. The mixture was stirred at 30° C. until a conversion of about 47% (HPLC) was reached. It was then filtered, concentrated to dryness and the resulting mixture was investigated by HPLC (Chiralpak AD 250×4.6, n-hexane+EtOH 6+1, flow 1 ml min, 25° C., 220/240 nm): ee of the (R)-butyric acid ester: 88%; ee of the (S)-alcohol: 97%.

Example 6

10 mg of the caproic acid ester [compound of the formula I where $R^1=COR^2$ and $R^2=CO(CH_2)_4CH_3$] were introduced into 1 ml of potassium phosphate buffer (0.1 M, pH=7.0)/dimethoxyethane (5:1). 5 mg of PLE were added. The mixture was stirred at 30° C. until a conversion of about 40% (HPLC) was reached. It was then filtered, concentrated to dryness and the resulting mixture was investigated by HPLC (Chiralpak AD 250×4.6, n-hexane+EtOH 6+1, flow 1 ml/min, 25° C., 220/240 nm): ee of the (R)-caproic acid ester: 66%; ee of the (S)-alcohol: 96%.

Example 7

10 mg of the caproic acid ester [compound of the formula I where $R^1=COR^2$ and $R^2=CO(CH_2)_4CH_3$] were introduced into 1 ml of potassium phosphate buffer (0.1 M, pH=7.0)/dimethoxyethane (5:1). 5 mg of cholesterol esterase from bovine pancreas were added. The mixture was stirred at 30° C. until a conversion of about 50% (HPLC) was reached. It was then filtered, concentrated to dryness and the resulting mixture was investigated by HPLC (Chiralpak AD 250×4.6, n-hexane+EtOH 6+1, flow 1 ml/min, 25° C, 220/240 nm): ee of the (R)-caproic acid ester: >99.8%; ee of the (S)-alcohol: >99.8%.

Example 8

10 mg of the capric acid ester [compound of the formula I where $R^1=COR^2$ and $R^2=CO(CH_2)_8CH_3$] were introduced into 1 ml of potassium phosphate buffer (0.1 M, pH=7.0)/dimethoxyethane (5:1). 5 mg of PPL were added. The mixture was stirred at 30° C. until a conversion of about 10% (HPLC) was reached. It was then filtered, concentrated to dryness and the resulting mixture was investigated by HPLC (Chiralpak AD 250×4.6, n-hexane+EtOH 6+1, flow 1 ml/min, 25° C., 220/240 nm): ee of the (R)-capric acid ester:>11 %; ee of the (S)-alcohol: 95%.

Example 9

10 mg of the butyric acid ester [compound of the formula I where $R^1=COR^2$ and $R^2=CO(CH_2)_2CH_3$] were introduced into 1 ml of potassium phosphate buffer (0.1 M, pH=7.0)/dimethoxyethane (5:1). 5 mg of horse liver acetone powder were added. The mixture was stirred at 30° C. until a conversion of about 46% (HPLC) was reached. It was then filtered, concentrated to dryness and the resulting mixture was investigated by HPLC (Chiralpak AD 250×4.6, n-hexane+EtOH 6+1, flow 1 ml/min, 25° C., 220/240 nm): ee of the (R)-butyric acid ester: 82%; ee of the (S)-alcohol: 96%.

What is claimed is:

1. A process for the kinetic resolution of racemates of a compound of the formula (I),

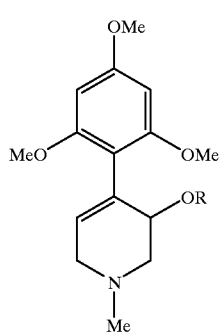

(I)

which comprises subjecting enantiomer mixtures or racemic mixtures of the compound of the formula (I), in which R is $COR^1$ where $R^1=(C_1-C_{16})$-alkyl, $(C_2-C_{16})$-alkenyl or $(C_3-C_{16})$-alkynyl, $C_nH_{2n}$-cycloalkyl where n=1–16, which can be branched or unbranched and which can be substituted by 1–3 substituents from the group F, Cl, Br, I, $CF_3$, CN, $NO_2$, hydroxyl, methoxy, ethoxy and $COOR^2$, where $R^2=(C_1-C_4)$-alkyl or $(C_2-C_4)$-alkenyl, which can be branched or unbranched and which can be substituted by 1–3 substituents from the group consisting of F, Cl, Br, and $CF_3$, in homogeneous or heterogeneous, aqueous, aqueous/organic or organic media in the presence of an enzyme, to a stereoselective hydrolysis or alcoholysis at a temperature of 10–80° C., optionally in the presence of one or more cosolvents and of a buffer and, after the reaction has taken place, separating the unreacted ester and the alcohol formed.

2. The process for the kinetic resolution of racemates of a compound of the formula (I), as claimed in claim 1, wherein R is $COR^1$ where $R^1=(C_1-C_{12})$-alkyl, $(C_2-C_{12})$-alkenyl or $(C_3-C_{12})$-alkynyl, $C_nH_{2n}$-cycloalkyl where n=1–12, which can be branched or unbranched and which can be substituted by 1–3 substituents from the group consisting of F, Cl, Br, $CF_3$, CN, $NO_2$, hydroxyl, methoxy, ethoxy and $COOR^2$, where $R^2$=methyl, ethyl or vinyl, which can be substituted by 1–3 substituents from the group consisting of F, Cl, and $CF_3$.

3. The process for the kinetic resolution of racemates of a compound of the formula (I), as claimed in claim 1, wherein R is $COR^1$ where $R^1=(C_1-C_{10})$-alkyl, $(C_2-C_{10})$-alkenyl or $(C_3-C_{10})$-alkynyl, $C_nH_{2n}$-cycloalkyl, where n=1–10, which can be branched or unbranched and which can be substituted by 1–3 substituents from the group consisting of F, Cl, Br, $CF_3$, CN, $NO_2$, methoxy, and $COOR^2$, where $R^2$=methyl, ethyl or vinyl, which can be substituted by 1–3 substituents from the group consisting of F, Cl, and $CF_3$.

4. The process for the kinetic resolution of racemates of a compound of the formula (I) as claimed in claim 1, wherein R is $COR^1$ where $R^1=(C_1-C_{10})$-alkyl, $(C_2-C_{10})$-alkenyl or $(C_3-C_{10})$-alkynyl, which can be branched or unbranched and which can be substituted by 1–3 substituents from the group consisting of F, Cl, Br, $CF_3$, and methoxy.

5. The process for the kinetic resolution of racemates of a compound of the formula (I) as claimed in claim 1, wherein the enzyme is a lipase, esterase or protease enzyme.

6. The process for the kinetic resolution of racemates of a compound of the formula (I) as claimed in claim 1, wherein the reaction mixture contains 2–50% by weight of ester.

* * * * *